United States Patent
Lopez Quintela et al.

(10) Patent No.: US 9,718,298 B2
(45) Date of Patent: Aug. 1, 2017

(54) USE OF LUMINESCENT NANOSYSTEMS FOR AUTHENTICATING SECURITY DOCUMENTS

(75) Inventors: Manuel Arturo Lopez Quintela, Ames (ES); Vicente Garcia Juez, Madrid (ES)

(73) Assignees: FABRICA NACIONAL DE MONEDA Y TIMBRE—REAL CASA DE LA MONEDA, Madrid (ES); NANOGAP SUB-NM POWDER, SOCIEDAD ANONIMA, Ames (ES)

( * ) Notice: Subject to any disclaimer, the term of this patent is extended or adjusted under 35 U.S.C. 154(b) by 173 days.

(21) Appl. No.: 14/125,938

(22) PCT Filed: Jun. 14, 2012

(86) PCT No.: PCT/EP2012/061353
§ 371 (c)(1),
(2), (4) Date: Dec. 12, 2013

(87) PCT Pub. No.: WO2012/172018
PCT Pub. Date: Dec. 20, 2012

(65) Prior Publication Data
US 2014/0103226 A1    Apr. 17, 2014

Related U.S. Application Data

(60) Provisional application No. 61/524,290, filed on Aug. 16, 2011.

(30) Foreign Application Priority Data

Jun. 15, 2011   (EP) ..................................... 11382200

(51) Int. Cl.
*G01N 21/64*   (2006.01)
*B42D 25/373*   (2014.01)
(Continued)

(52) U.S. Cl.
CPC ........... *B42D 25/373* (2014.10); *B41M 3/144* (2013.01); *B42D 25/21* (2014.10); *B42D 25/23* (2014.10);
(Continued)

(58) Field of Classification Search
CPC ........ G21K 5/00; B42D 25/26; B42D 25/387; B42D 25/382; B42D 2033/10;
(Continued)

(56) References Cited

U.S. PATENT DOCUMENTS

2002/0021003 A1   2/2002   McGrew
2005/0001038 A1   1/2005   Walter et al.
(Continued)

FOREIGN PATENT DOCUMENTS

IN   WO 2012090034 A1 *   7/2012   ............. B82Y 30/00

OTHER PUBLICATIONS

Das, R., et al., "Preparation of linoleic acid capped gold nanoparticles and their spectra", "Physica E", Jul. 18, 2010, pp. 224-227, vol. 43.
(Continued)

*Primary Examiner* — David Porta
*Assistant Examiner* — Gisselle Gutierrez
(74) *Attorney, Agent, or Firm* — Hultquist, PLLC; Steven J. Hultquist

(57) ABSTRACT

The present invention relates to the use of nanosystems as non deactivable security markers comprising metal atomic quantum clusters (AQCs) of at least two different size distributions encapsulated in a cavity with an inner diameter less than or equal to approximately 10 nm. These nanosystems are luminescence, particularly fluorescence after external excitation. The invention also relates to security docu-
(Continued)

ments, articles or elements incorporating these markers as well as to a method and a system for detecting the same.

27 Claims, 5 Drawing Sheets

(51) Int. Cl.
*B42D 25/333* (2014.01)
*B42D 25/328* (2014.01)
*B42D 25/355* (2014.01)
*B42D 25/378* (2014.01)
*B42D 25/21* (2014.01)
*B42D 25/23* (2014.01)
*B41M 3/14* (2006.01)
*B82Y 15/00* (2011.01)
*D21H 21/48* (2006.01)
*G07D 7/12* (2016.01)
*C09K 11/02* (2006.01)
*C09K 11/58* (2006.01)
*D21H 19/02* (2006.01)
*D21H 21/52* (2006.01)
*D21H 21/54* (2006.01)
*C09D 5/22* (2006.01)
*G06K 19/14* (2006.01)
*G21K 5/00* (2006.01)
*B42D 25/29* (2014.01)
*G07D 7/1205* (2016.01)
*B42D 25/382* (2014.01)
*B42D 25/387* (2014.01)

(52) U.S. Cl.
CPC ........... *B42D 25/29* (2014.10); *B42D 25/328* (2014.10); *B42D 25/333* (2014.10); *B42D 25/355* (2014.10); *B42D 25/378* (2014.10); *B82Y 15/00* (2013.01); *C09D 5/22* (2013.01); *C09K 11/02* (2013.01); *C09K 11/025* (2013.01); *C09K 11/58* (2013.01); *D21H 19/02* (2013.01); *D21H 21/48* (2013.01); *D21H 21/52* (2013.01); *D21H 21/54* (2013.01); *G01N 21/64* (2013.01); *G06K 19/14* (2013.01); *G07D 7/12* (2013.01); *G07D 7/1205* (2017.05); *G21K 5/00* (2013.01); *B42D 25/382* (2014.10); *B42D 25/387* (2014.10); *B42D 2033/10* (2013.01); *B42D 2033/32* (2013.01); *B42D 2035/34* (2013.01)

(58) Field of Classification Search
CPC ........... B42D 2035/34; B42D 2033/32; G01N 21/64; C09D 5/22; G06K 19/14; D21H 21/54; D21H 21/52; D21H 19/02; D21H 21/48; C09K 11/02; C09K 11/025; C09K 11/58; G07D 7/122; G07D 7/12; B82Y 15/00; B41M 3/144
USPC .............. 250/459.1, 216, 458.1; 252/301.36; 283/85; 427/157
See application file for complete search history.

(56) References Cited

U.S. PATENT DOCUMENTS

2007/0138295 A1 6/2007 White
2007/0275244 A1 11/2007 Handrosch et al.
2008/0265176 A1 10/2008 Chauhan et al.
2009/0035852 A1 2/2009 Lopez Quintela et al.
2009/0206162 A1 8/2009 De Cremer et al.
2010/0140501 A1 6/2010 Lawandy
2011/0305919 A1 12/2011 Conroy et al.
2012/0187341 A1 7/2012 Strek et al.

OTHER PUBLICATIONS

Douliez, J., et al., "Synthesising gold nanoparticles within bola fatty acid nanosomes", "Journal of Colloid and Interface Science", May 27, 2009, pp. 610-613, vol. 337
Zheng, J., et al., "Individual Water-Soluble Dendrimer-Encapsulated Silver Nanodot Flourescence", "J. Am. Chem. Soc.", Oct. 31, 2002, pp. 13982-13983, vol. 124.
Zheng, J., et al., "Highly Fluorescent, Water-Soluble, Size-Tunable Gold Quantum Dots", "Phys. Rev. Lett.", Aug. 13, 2004, pp. 077402-1-077402-4, vol. 93, No. 7

* cited by examiner

USE OF LUMINESCENT NANOSYSTEMS FOR AUTHENTICATING SECURITY DOCUMENTS

CROSS-REFERENCE TO RELATED APPLICATIONS

This application is a U.S. national phase under the provisions of 35 U.S.C. §371 of International Patent Application No. PCT/EP12/61353 filed Jun. 14, 2012, which in turn claims priority of European Patent Application No. 11382200.1 filed Jun. 15, 2011 and the benefit of priority of U.S. Provisional Patent Application No. 61/524,290 filed Aug. 16, 2011. The disclosures of such international patent application and both European and U.S. provisional priority patent applications are hereby incorporated herein by reference in their respective entireties, for all purposes.

FIELD OF THE INVENTION

The present invention relates to nanosystems comprising metal atomic quantum clusters (AQCs) for the use thereof as carriers of authentication or anti-forgery features in security documents or articles.

BACKGROUND

As demonstrated by the huge number of patents existing in this field, the use of different security elements making the forgery of documents difficult has been extended in recent years. Some of these elements are detectable by human beings, meanwhile other security elements which are incorporated into documents require the use of special tools for detection thereof. These tools include spectroscopic methods such as UV-VIS absorption spectroscopy, fluorescence emission spectroscopy, IR spectroscopy or Raman spectroscopy.

Thus, luminescence pigments or substances have been incorporated into various security documents for certifying the authenticity thereof, the detection or observation of which requires the use of an excitation light in a particular region of wavelengths (for example UV light).

Today, the only fluorescent systems known having huge Stokes' displacement of greater than 200 nm and slow decaying times of more than microsecond are based on rare earth ions. However, they present multiple drawbacks such as: the difficulty in incorporating thereof in matrices such that they do not lose their fluorescent characteristics; the existence of fixed and particular excitation, emission and Stokes' displacement characteristics corresponding to each rare earth, therefore they are not susceptible to being changed, and they are expensive and scarce materials. Examples of these rare earth luminescent systems as security markers are described in documents U.S. Pat. No. 4,598,205, U.S. Pat. No. 4,452,843 and U.S. Pat. No. 4,463,970.

An example for the synthesis of nanosystems is described in Gaillard et al, *Journal of Colloid & Interface Science*, 2009, 337, 610-613.

Therefore, there is a clear need to develop new compositions and methods which make forging security documents difficult.

BRIEF DESCRIPTION OF THE INVENTION

The authors of the present invention have discovered fluorescent nanosystems with huge Stokes' shifts and decaying times much greater than those described in the state of the art which do not use rare earth elements. These nanosystems comprise an inner cavity, or nanocavity, where metal atomic quantum clusters (AQCs) of at least two different sizes preferably of transition metals are encapsulated. The inner surface of this inner cavity is functionalized to enable suitably stabilizing the AQCs and said cavity has a nanometric inner diameter allowing the distance between the AQCs of at least two different sizes present in said nanocavity to be less than or equal to approximately 10 nm. Without being bound to any particular theory, it is believed that this allows it to give Förster resonance energy transfer (FRET) producing luminescence. Since these nanocavities have an inner diameter smaller than the Förster distance, a distance less than or equal to 10 nm, and given that only active species are present in said nanocavities, the deactivation of luminescence particularly of fluorescence is prevented, being able to achieve with these systems high quantum yields which are greater than those obtained with the rare earth-based systems.

The excitation and emission wavelengths depend on the size of the AQCs present in the nanocavity of the nanosystem. Therefore, the excitation and emission wavelengths can be selected at will directing the formation of AQCs of necessary sizes so that FRET is given between the AQCs of at least two different sizes in said nanocavity. To optimize the FRET, the emission wavelength ($\lambda_{em}$) of the small AQC or the smaller sized AQC which is the AQC that acts like a donor must be overlapped, as much as possible, with the excitation of the large AQC or the larger sized AQC which is the AQC that acts like an acceptor. Thus the Stokes shift to be obtained can be selected at will, thus releasing the fixed and particular imposition that exists in rare earth-based fluorescence methods. Furthermore, due to the characteristics of the AQCs used there is no photobleaching and the use of the FRET process as the basis of the proposed method ensures long fluorescence decaying times of more than a microsecond.

Metal transition elements or combinations thereof can be used. Furthermore, the great natural abundance of these elements makes this a completely sustainable method. The luminescent nanosystems synthesized:
- are stable in the pH range of 3 to 10,
- can be concentrated until dry without losing their fluorescent properties even in dried form, and also
- can be redissolved once dried without losing their fluorescent properties, and also
- are used at a concentration less than that used in rare earth element-based luminescent systems.

The nanosystem can be further functionalized in its outer surface for the use thereof in different environments so that it can be used as a marker for security elements, articles or documents regardless of the support thereof.

Therefore, a first aspect of the present invention consists of the use of nanosystems comprising metal atomic quantum clusters (AQCs) of at least two different sizes encapsulated in a cavity with an inner diameter less than or equal to approximately 10 nm as a marker for a security document, article or element.

In a second aspect, the invention relates to a security article, document or element comprising metal atomic quantum clusters (AQCs) of at least two different sizes encapsulated in a cavity with an inner diameter less than or equal to approximately 10 nm.

In a third aspect, the invention relates to a method for the incorporation of a nanosystem comprising metal atomic quantum clusters (AQCs) as defined previously in a security document or article wherein said incorporation is performed:

(i) during the manufacturing of the material used to make said article or document;

(ii) as part of an additive which is added to said security article or document;

(iii) on the surface of said article or document, or (iv) as a part of one or more of the dyes or inks used in the manufacturing of the security document or article.

Likewise, the invention relates to a method for determining the authenticity of a security document, article or element as has been defined previously which comprises:

a) irradiating the security document, article or element with an external excitation source at a pre-determined excitation wavelength ($\lambda_{exc.}$) to excite the nanosystem, and b) detecting one or more of the following parameters:
emission wavelength ($\lambda_{em.}$),
intensity,
mean lifetime,
anisotropy,
of said nanosystem by suitable detection means.

In another aspect, the invention relates to a system for determining the authenticity of a security document, article or element as has been defined previously which comprises:

a positioner wherein the security document, article or element is placed;

means which allow focusing, transmitting and optionally amplifying the excitation originating from an external excitation source on the part of the document, article or element to be irradiated; and suitable detection means for measuring one or more of the following parameters: emission wavelength ($\lambda_{em.}$), intensity, mean lifetime or anisotropy.

DETAILED DESCRIPTION OF THE INVENTION

Figure 1:
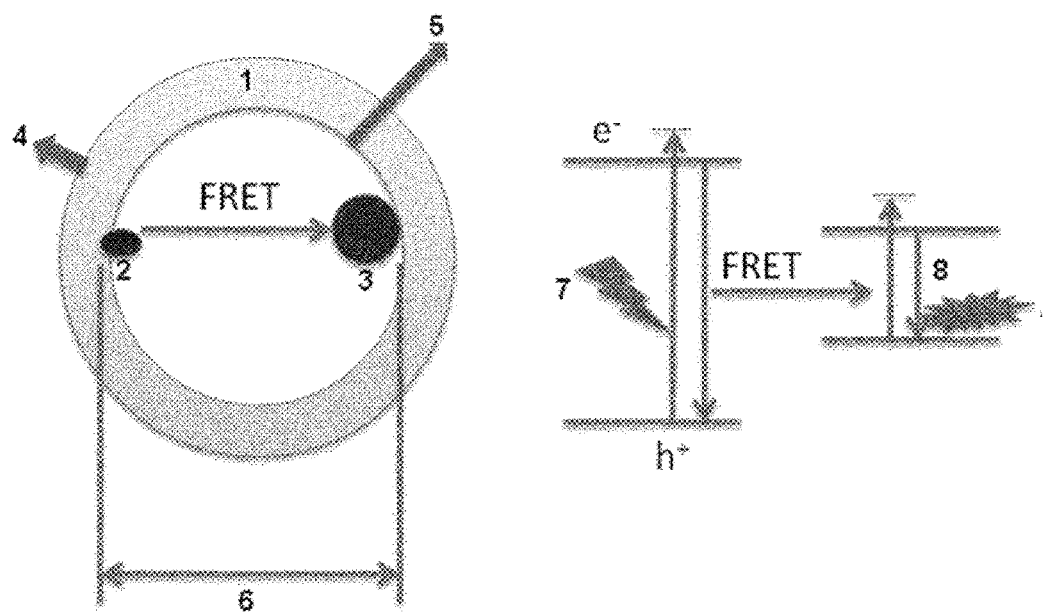
FIG. 1 shows a schematic depiction of the invention wherein the numbers refer to: 1. nanosystem; 2. small AQC or donor; 3. large AQC or acceptor; 4. functionalization of the outer surface of the nanosystem; 5. functionalization of the inner cavity; 6. inner diameter of the nanocavity which is within of the range of Förster distance of approximately 10 nm or less; 7. excitation of the electrons to higher energy levels ($\lambda_{exc.}$); 8. emission ($\lambda_{em.}$); and the arrow indicates the presence of Förster resonance energy transfer (FRET).

The meanings of the following terms of the present invention are detailed below.

Nanosystems

The term "nanosystem" refers to an spheroid-like nanometric supramolecular structure formed by one or two layers of amphiphilic molecules, wherein said amphiphilic molecules form a nanocavity at the inside of the nanosystem. Particularly, the nanosystem having an outer diameter approximately equal to or less than 20 nm, preferably equal to or less than 18 nm and more preferably equal to or less than 15 nm. The inside of the nanosystem comprised at least one nanocavity with an inner diameter less than or equal to 10 nm, preferably less than or equal to approximately 5 nm, more preferably between 0.8 and 4 nm. In a particular embodiment, the inner diameter of the nanocavity is between approximately 1.5-1.8 nm. Non-limiting examples of nanosystems are nanosomes, micelles or reverse micelles.

The expression "spheroid-like" means that it has a solid geometrical figure similar in shape to a sphere.

The amphiphilic molecules forming the nanosystems may be the same or different, preferably two different type of molecules, and each molecule possess both hydrophilic and lipophilic properties.

The lipophilic properties are given by a group which is typically a hydrocarbon moiety, such as an aliphatic chain of the form $CH_3$—$(CH_2)_n$— or —$(CH_2)_n$— being 30>n>2, preferably 20>n>10.

The hydrophilic properties are given by a hydrophilic group. The hydrophilic group may be a charged group or a polar uncharged group. The charged group is selected from anionic groups, preferably is selected from the group formed by carboxylates, sulfates, sulfonates and phosphates. The polar uncharged group is selected from the group formed by —OH, —SH, —NH$_2$, —NH—, —Cl, —PH$_3$, —SR, —OR, —NR$_2$, —NHR and —NR—, wherein R represents an organic alkyl group of a short hydrocarbon chain, C$_1$-C$_4$, preferably methyl, ethyl or propyl group.

The amphiphilic molecules may have one aliphatic CH$_3$—(CH$_2$)$_n$— chain and one hydrophilic group bound to it or two hydrophilic groups bound each one at each end of the aliphatic —(CH$_2$)$_n$— chain.

The term "nanosome" in the scope of the present invention relates to a nanometric sized vesicle artificially prepared and formed by a lipid layer. Thus, the term "nanosome" refers to an spheroid nanometric supramolecular structure formed by one layer of amphiphilic molecules (lipids) having two hydrophilic groups bound each one at each end of the aliphatic —(CH$_2$)$_n$— chain, or at the antepenultimate, χ, or penultimate, ψ, positions of the aliphatic CH$_3$—(CH$_2$)$_n$— chain.

Therefore, the lipids forming said monolayer in the nanosomes of the invention comprise (see FIG. 2):
a hydrophilic group such as a carboxyl (COO$^-$) or phosphate (PO$_4^-$) group, for example, that are on the outer surface of the vesicle, at one end of the aliphatic chain and
substituted at the antepenultimate, χ, penultimate, ψ, positions of the aliphatic CH$_3$—(CH$_2$)$_n$— chain, or last, ω, positions of the aliphatic —(CH$_2$)$_n$— chain with groups such as for example —OH, —SH, —NH$_2$, —NH—, —Cl, —PH$_3$, —SR, —OR, —NR$_2$, —NHR, or —NR—, wherein R represents an organic group of a short hydrocarbon chain, C$_1$-C$_4$, capable of forming nanosomes which are located towards the inside of the vesicle, at the other end of the aliphatic chain or at the ultimate positions of said aliphatic chain with respect to hydrophilic group, said groups forming the nanocavity with an inner diameter less than or equal to 10 nm, preferably less than or equal to approximately 5 nm, more preferably between 0.8 and 4 nm. In a particular embodiment, the inner diameter of the nanocavity is between approximately 1.5-1.8 nm.

The term "micelle" refers to amphiphilic molecules aggregates. In an aqueous medium, the lipophilic domains of the molecule aggregate are oriented towards the inside of the micelle and the hydrophilic domains are in contact with the medium. In "reverse micelles" the molecules are organized such that the lipophilic region is exposed to the outside and the hydrophilic region to the inside.

In a particular embodiment the nanosystem is selected from the group formed by a nanosome, micelle and reverse micelle, preferably the nanosystem is a nanosome.

In the particular embodiment wherein the nanosystem is a nanosome, the nanosome comprises ω-hydroxyacids (HO—(CH$_2$)$_m$—COOH) and ω-mercaptoacids (HS—(CH$_2$)$_p$—COOH) where m and p have a value between 2 and 30, preferably m and p have a value between 10 and 20. In a particular embodiment m and p have a value of 15. The value of m and p can be different or the same. In the event that m and p are different the difference between them is less than 6 carbons, preferably the difference of the values of m and p is between 1 and 4. In a preferred embodiment m and p are the same. The ω-hydroxyacids and ω-mercaptoacids present in the nanosome are forming a spherical monolayer with the acid groups, —COOH, (or —COO$^-$, if the salt of the corresponding acid is used) directed towards the outer surface of the nanosystem and the —OH and —SH groups directed towards the inside forming an inner cavity in the nanosome such that two approximately concentric spheres are formed, or as referred to in the literature, in the form of fatty acids "bola". This spherical monolayer can have a thickness between approximately 2-10 nm, preferably approximately 5 nm.

In the particular embodiment wherein the nanosystem is a reverse micelle, the reverse micelle comprises at least two different surfactants, wherein at least one comprises a thiol or thioether group as its polar group. In a more particular embodiment, the at least two surfactants are an alcohol ethoxylate and a ω-mercaptoacid. The inner cavity of the nanosystem is closed. As mentioned above, the inner diameter of said inner cavity is less than or equal to 10 nm, preferably less than or equal to approximately 5 nm and more preferably the inner diameter of said inner cavity is between approximately 0.8 and 4 nm. In a particular embodiment the diameter of this inner nanocavity is between approximately 1.5-1.8 nm. In the particular embodiment of the nanosomes, said nanocavity is formed by hydroxyl, —OH, and mercapto, —SH, groups, however exchanging these functional groups with others that also interact with the metals, such as —NH$_2$, —NH—, —Cl, —PH$_3$, —SR, —OR, —NR, —NHR, —NR—, where R represents an organic group of a short hydrocarbon chain, C$_1$-C$_4$, capable of forming nanosomes, is possible.

A particular example of these nanosomes is described in Gaillard, C., *Journal of Colloid and Interface Science*, Vol. 337, 2, 610-613, which describes gold particle synthesis inside these nanosystems.

The term "Atomic Quantum Cluster", abbreviated as AQC, is understood, as said before, as metal Atomic Quantum Cluster. Metal Atomic Quantum Clusters are formed exclusively by zero-oxidation-state metal atoms, M$_n$, with less than 200 metal atoms (M$_n$, n<200) and with a size of less than 2 nm. The AQCs are stable over time.

The nanosystem described comprises, inside the inner cavity thereof, i.e., encapsulated, atomic quantum clusters, which are known for being a family of zero-valent metals which do not longer behave like a "metal" and their behaviour becomes molecular like. Therefore, new properties which are not observed in the nanoparticles, microparticles or metal materials in mass appear in these clusters. Therefore, the physical-chemical properties of the AQC cannot be simply extrapolated from those of the nano/microparticles.

In the present invention said AQCs encapsulated inside the mentioned inner cavity are formed by metal elements, M$_n$, of transition metals or the bimetal combinations thereof and are present in the nanosystem in at least two different sizes where n is the number of metal atoms present, n has a value of:
between 2 and 309 metal atoms (M$_n$, 2≤n≤309),
between 2 and 102 metal atoms (M$_n$, 2≤n≤102),
between 2 and 55 metal atoms (M$_n$, 2≤n≤55), or
between 2 and 25 metal atoms (M$_n$, 2≤n≤25).

The AQCs of the invention have sizes comprised between approximately 0.3 and 2.2 nm, preferably between approximately 0.3 and 2 nm, more preferably between approximately 0.3 and 1.8 nm.

Figure 2:
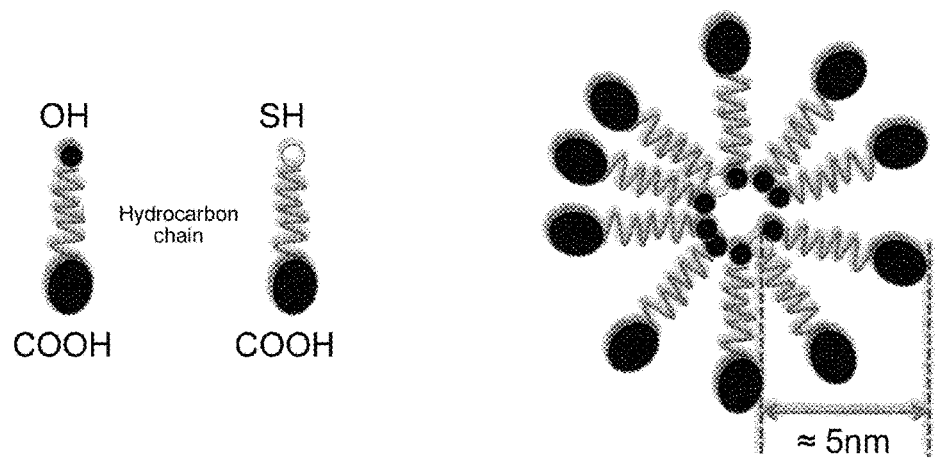
FIG. 2 shows a schematic depiction of the nanosystem particularly a nanosome where the ω-hydroxyacids and ω-mercaptoacids form the monolayer of the nanosome wherein the monolayer has an approximate thickness of 5 nm, it is observed that the acid groups form the outer surface of the nanosome and the hydroxyl, OH, and mercapto, SH, groups face inwards forming the surface of the inner cavity of the nanosome.
Figure 3:
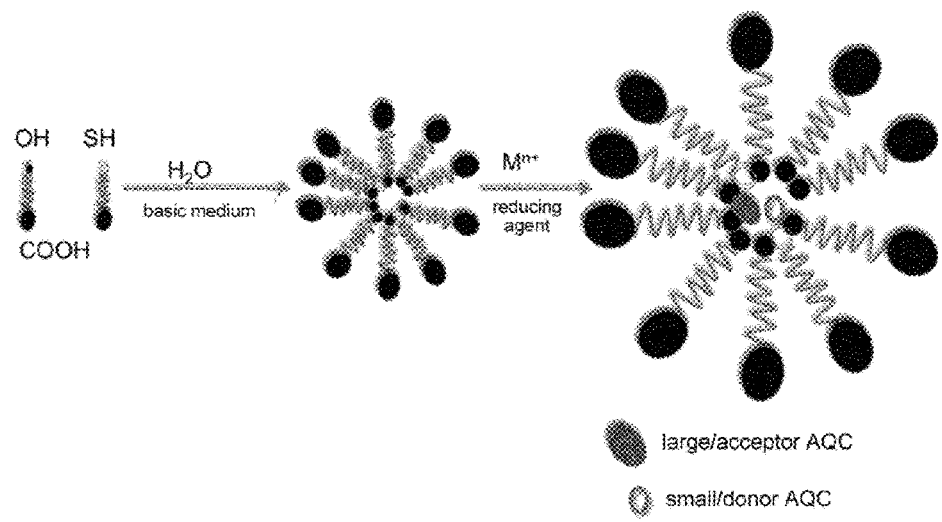
FIG. 3 shows a schematic depiction of the formation of the AQCs inside the nanosystem particularly inside the nanosomes of Examples 1 and 2. In a first step, the ω-hydroxyacids and ω-mercaptoacids in the presence of a basic medium form the nanosome in water. In a second step, the transition metal or combination of metals which will produce small AQCs or donors and large AQCs or acceptors by means of reduction, is added. The example is schematic showing only one AQC of each type, but there may be a varied number of both inside the cavity.

The presence of at least two different sizes in the inner nanocavity of AQCs is what allows using the nanosystems described as luminescent nanosystems. The presence of OH and SH groups in the inner cavity of the nanosome allows selecting the production of the at least two types of clusters and their sizes, i.e., by varying the OH/SH ratio the size of the two types of clusters produced as schematically seen in FIGS. 2 and 3 can be selected.

The sizes of the clusters to be synthesized are determined by the [mercapto]/[M]=R1 and [hydroxyl]/[mercapto]=R2 concentration ratio.

The R1 ratio determines the size of the smaller cluster, the donor cluster, such that an increase of the ratio decreases the size of the smaller clusters produced ("arrested growth").

The R2 ratio determines the size of the larger cluster (acceptor cluster), such that an increase of this ratio increases the size of the larger clusters produced.

The expression "different size" of the AQCs refers to the fact that the at least two AQCs are different in number by at least three metal atoms. Preferably they are different by at least four metal atoms. More preferably they are different by at least five metal atoms.

Without being bound to any particular theory, it is believed that luminescence is produced by the Förster resonance energy transfer (FRET) involving the energy absorbance by a fluorophore at an excitation wavelength ($\lambda_{exc.}$) followed by the emission by another fluorophore at an emission wavelength ($\lambda_{em.}$) greater than the excitation wavelength, i.e., $\lambda_{em.} > \lambda_{exc.}$. The interaction to produce FRET only happens at very short distance, less than or equal to approximately 10 nm, between two electronic excitation states of two fluorescents molecules in which the emission wavelength of one of them coincides with the excitation wavelength of the other. This excitation energy is transferred through a dipole-dipole intermolecular bonding without radiation. Both wavelengths, $\lambda_{exc.}$ and $\lambda_{em.}$, are separated by tens or hundreds of nanometers. This wavelength difference is what is known as Stokes shift, $\delta_{stokes} = \lambda_{em} - \lambda_{exc}$.

Therefore, in the scope of the present invention, in order to produce luminescence through Förster resonance energy transfer (FRET) between the AQCs of at least two different sizes, the smaller sized AQC or excitation cluster which acts like a donor AQC receives the external excitation at a particular excitation wavelength, it therefore goes into an excited electronic state. This excitation energy is transferred to the acceptor AQC or emission cluster which is at a distance less than or equal to 10 nm Föster distance, as schematically depicted in FIG. 1.

An approximate estimation of the cluster excitation and emission wavelengths can be determined by approximation by means of the Jellium model (see J. Calvo et al., *Encyclopedia of Nanotechnology*, Ed. by B. Bhushan, Springer Verlag, 2011, for example). This model predicts in a rather approximate manner the prohibited energy bandgap of the clusters and, therefore, the position of the emission bandgap thereof. The excitation bandgap of the clusters can in turn be predicted from the emission bandgap taking into account that the Stokes shift in clusters of a particular size is of approximate 50-100 nm. The following table, Table 1, shows the theoretical data for AQCs of Au or Ag according to this mode, i.e., the approximate excitation $\lambda_{exc.}$, and emission, $\lambda_{em.}$, wavelengths have been calculated with an error of ±50 nm in AQCs of Au or Ag by means of said Jellium model: $E_{em} = E_F/N^{1/3}$; where $E_{em}$=emission energy; N=no. of atoms in the AQC; and $E_F$=Fermi level which is the same approximately 5.5 eV for gold and silver.

TABLE 1

| Cluster | $\lambda_{exc.}$ (nm) | $\lambda_{em.}$ (nm) |
|---|---|---|
| $A_2$ | 200-250 | 300 |
| $A_3$ | 240-290 | 340 |

TABLE 1-continued

| Cluster | $\lambda_{exc.}$ (nm) | $\lambda_{em.}$ (nm) |
|---|---|---|
| $A_4$ | 270-320 | 370 |
| $A_5$ | 300-350 | 400 |
| $A_6$ | 325-375 | 425 |
| $A_7$ | 350-400 | 450 |
| $A_{10}$ | 400-450 | 500 |
| $A_{12}$ | 440-490 | 540 |
| $A_{15}$ | 475-525 | 575 |
| $A_{20}$ | 535-585 | 635 |
| $A_{25}$ | 580-630 | 680 |
| $A_{30}$ | 630-680 | 730 |
| $A_{40}$ | 700-750 | 800 |

These values can also vary in practice when the nanosystem is made to react to exchange the OH and SH groups with other ligands in the inner cavity of the nanosystem. Without being limiting, the ligands to be exchanged can be chosen from —$NH_2$, —NH—, —Cl, —$PH_3$, —SR, —OR, —$NR_2$, —NHR, —NR—, where R represents a short chain organic group capable of forming nanosomes.

In the context of the present invention, the luminescent nanosystems described present Stokes shifts greater than approximately 150 nm, preferably greater than approximately 300 nm.

In other words, the type of clusters to be used to obtain a particular excitation and emission wavelength can be decided from the table above. Thus, for example, to obtain a system with an excitation wavelength at 300 nm, an emission wavelength at 550 nm and a Stokes shift of 250 nm, the following cluster sizes should be selected:

excitation cluster ("donor"): $A_3/A_4$,
emission cluster ("acceptor"): $A_{12}$.

The nanosystems described have functional groups in their exterior, for example, the nanosomes have COOH groups that can be used or functionalized, for example, for binding them to the substrate body or to the surface of the element, document or article, to be stable in the security composition comprising the security ink, etc.

Therefore an aspect of the present invention relates to the use of a nanosystem as described above comprising metal atomic quantum clusters (AQCs) of at least two different sizes encapsulated in a cavity with an inner diameter less than or equal to 10 nm, preferably less than or equal to 5 nm as a luminescent nanosystem, as a marker for a security document, article or element. Preferably a fluorescent nanosystem is used as a marker for a security document, article or element. The metal M of the AQCs is a transition metal or combination thereof. Preferably the transition metal is selected from Au, Ag, Co, Cu, Pt, Fe, Cr, Pd, Ni, Rh and combinations thereof, preferably is selected from Au, Ag, Cu and combinations thereof, and more preferably it is selected from Au, Ag and combination thereof. The nanosystems comprising atomic quantum clusters are referred to as the "luminescent nanosystems" throughout this text In the scope of this invention the term "combination of transition metals" refers to AQCs having atoms of at least two different transition metals as well as to the presence of AQCs of a single transition metal in the presence of AQCs of another transition metal different from the first. Therefore the at least two AQCs of different size can be AQCs of the same transition metal, AQCs of different transition metal, or AQCs of the same or different bimetal combination.

Documents, Articles and Elements of Security

In an additional aspect, the present invention relates to a security element which comprises nanosystems comprising atomic quantum clusters (AQCs) of at least two different size distributions encapsulated in a cavity with an inner diameter less than or equal to approximately 10 nm.

According to the present invention, the term security element relates to an element which is integrated into a security document or article for the purpose of authenticating it. The security element can be integrated into the security article or document in its body, such as for example in the substrate body, security threads, security fibers, watermarks, tactile effects, cellulose strips, layers of glues, lacquers, plasters, planchettes or other commonly used elements, or on its surface, such as for example holograms added in different bills and credit cards, security inks, plastic sheets or other commonly used elements.

In the scope of the present invention, "substrate" is understood as paper, polymer or polymer combination.

The security element can be randomly distributed or attached in specific positions of the document or article and gives security features to the document or article containing it, these features being able to be of a very diverse kind provided that their objective is to make the forging of the security documents or articles difficult or to facilitate the authentication thereof.

According to a particular embodiment, the security element is selected, for example from substrate body, security paper, security threads, security fibers, security inks, watermarks, tactile effects, cellulose strips, planchettes, holograms, security pigments or substances, and sheets. These security elements can be prepared incorporating the nanosystems or from the security compositions comprising the nanosystems by following the common methods known by the person skilled in the art.

In a particular embodiment of the invention, the nanosystems are deposited in supports with the form of fibers. Thus, it is possible to deposit said nanosystems on natural fibers, preferably cotton fibers, such that security fibers which are incorporated into the security element as part of the fibers themselves which form the security paper is provided.

In another particular embodiment, the luminescent nanosystems of the invention are deposited on support particles which in turn are incorporated into the formulation of an ink thus giving rise to security inks. In another embodiment, the nanosystems are directly incorporated into the formulation of an ink.

In a particular embodiment, the security element is formed by a security composition comprising a type of luminescent nanosystems of the invention, in another particular embodiment the security element is formed by a security composition comprising the combination of at least two types of luminescent nanosystems of the invention. In another particular embodiment, the security element is formed by the combination of at least two security compositions wherein each of said security compositions comprises one type of luminescent nanosystems of the invention as has been defined previously.

In another particular embodiment, the security element is formed by the combination of two security inks wherein each of said security inks comprises one type of luminescent nanosystems of the invention as has been defined previously. In this embodiment, the types of nanosystems comprised in both security inks have the same chemical composition but they have different AQCs size, i.e., they have different Stokes shift.

In another particular embodiment, the security element is formed by the combination of two security inks wherein each of said security inks comprises on type of luminescent nanosystems of the invention as has been defined previously. In this embodiment, the types of nanosystems comprised in both security inks have different chemical composition since the metals of the AQCs are different.

In the particular case of using inks, the security element is not only formed by a material with well defined properties in terms that it presents a specific Stokes shift, emission wavelength ($\lambda_{em}$), intensity, mean lifetime or anisotropy, rather also by a particular code, either a two dimensional image, an anagram or a binary code such as a barcode. This method simplifies the detection of the security element since the latter is located in a well defined region of the security document.

Additionally, these security elements can be used as markers for security articles or documents.

In another aspect, the invention also relates to a security article or document comprising the luminescent nanosystems of the invention as has been defined previously. Likewise, the invention relates to a security article or document comprising a security element as has been described previously.

According to the present invention, the term security article or document relates to those having particular characteristics which ensure their origin and therefore their authenticity. These security articles or documents include all of those used by public administrations and their public organizations as well as those used in the private sector when they circulate greatly between the group of citizens and companies, and containing identification, authentication or anti-forgery means or devices. Preferably, the security documents or articles are selected from identification documents such as identification cards, passports, passes and the like, and valuable documents such as bills, cheques, stamps, certificates and the like.

Preferably, the security article or document is selected from security paper, identification documents, banknotes, cheques, stamps and stamp-impressed paper, labels and tickets. More preferably, it is a security paper.

The luminescent nanosystems of the invention can be incorporated into the security article or document:
  (i) during the manufacturing of the material used to make said article or document;
  (ii) as part of an additive which is added to said article or document;
  (iii) on the surface of said article or document; or
  (iv) as a part of one or more of the dyes or inks used in the manufacturing of the security document or article.

In a particular embodiment, the luminescent nanosystems used in the invention can form part of a single security composition which is incorporated into the security article or document according to any one of method i)-iv) described previously.

The luminescent nanosystems of the invention can be added to the body of paper of the security documents as a dispersion forming part of the substrate body itself. Nevertheless, the incorporation thereof on the surface of the document as a hologram or as an inscribed security thread, or forming part of the glue or lacquer, is preferred. It can also be incorporated into polymer films such as polyvinyl alcohol films, for example, which can coat the security article or document. Likewise, the luminescent nanosystems can be incorporated into inks used for printing the security document, enabling forming imperceptible part of images, figures, legends, barcodes or elements for tactile labeling.

The functionalization of the nanosystems on microparticles further allows solving the problem where the nanosystems pass through the pores of the section of the substrate since the microparticles are retained in the substrate body due to their large size.

Thus, the sizes of nanosystems defined in the invention guarantee its incorporation and stay in the substrate preferably in the paper. Thus, the security document or article is provided with the code corresponding to the combination of selected luminescent nanosystems.

In a particular embodiment of the invention, the luminescent nanosystems are deposited in substrates with the form of fibers. Thus, it is possible to deposit said nanosystems on natural fibers, preferably cotton fibers, such that security fibers are directly incorporated into the security material as part of the fibers themselves which form the paper is provided.

In another particular embodiment, the luminescent nanosystems are deposited on microparticles where the latter in turn are incorporated into the substrate body or are incorporated into the formulation of the ink itself, thus forming security inks as has been mentioned previously for the security elements.

In a particular embodiment, the percentage of the luminescent nanosystems of the invention incorporated into the security document, article or element is less than 5% by weight, preferably less than 1% by weight, and greater than 0.001% by weight of the total weight of the security document or article. This low concentration makes the compositional identification by techniques used such as chemical analysis, X-ray diffraction, spectroscopic techniques or the like difficult. Nevertheless, the identification of the composition does not represent the security marker therein since the specific response is achieved by the external excitation of the luminescent nanosystems by measuring the emission transmitted by said nanosystems after said excitation or by measuring any other parameters characteristics of the luminescent nanosystems of the invention.

The number of different security markers increases with the number of different AQC sizes, transition metals and the combination thereof used which are characterized by their chemical composition as well as by the size of the nanosystems, therefore, the number of different security markers that can be generated is virtually limitless. This allows generating encoded security markers such that a particular security marker corresponds to the documents that have been created at a particular time, or for a particular value or a particular purpose, or by a particular organism, therefore making the security documents traceable and further increasing the security thereof.

The security compositions comprising the luminescent nanosystems of the invention are always active, a security composition not showing luminescence after the application of an external excitation not being possible. Thus, it is impossible that a security document can be falsified by not having the features corresponding to the security composition. Likewise, the luminescence response of the materials comprised in the security compositions cannot be modified without the security document which the materials form a insoluble part being destroyed, therefore the security compositions are characterized by being permanent and non deactivable.

The luminescent nanosystems used in the invention are formed by very stable materials, not being sensitive generally to oxidation or hydration processes. Nevertheless, the nanosystems can sometimes be coated with layers of inert materials such as alumina, glasses, silicates, or other oxide materials for protecting them from the environment. In the same manner, the nanosystems could also be coated with polymers or other organic materials to improve their adherence to the fibers of the paper or for their improved transmission in the event that they form part of inks.

The combination of the luminescent nanosystems of the invention described in the present invention allows efficiently labeling the security articles or documents, presenting a safe coding system. The security compositions described are permanent, non deactivable and have an encoded response which requires the use of a detection system designed for such purpose.

Authentication Method

In another aspect, the invention relates to a method for determining the authenticity of a security document or article which comprises measuring the luminescence of said security document or article to determine the presence of the security marker, i.e., to determine the presence of the nanosystems presenting luminescence, preferably fluorescence.

Since no other molecules are present in the inner nanocavity of the nanosystem, the energy does not dissipate or lost, i.e., the luminescence is maintained. In a particular embodiment, there is no blinking or photobleaching for at least 500 minutes exciting the samples at 300 nm every 30 seconds.

In a particular embodiment, the emission lifetime ($\tau$) can be measured. The emission lifetime ($\tau$) which is the luminescence extinction time or the mean lifetime which is the time lapsed since the end of the excitation until the emission intensity reduces to 1/e of the maximum intensity value, i.e., until it reduces to approximately 37%. In an embodiment of the present invention the mean lifetime of the luminescence, preferably fluorescence, is greater than 0.1 μs, preferably greater than 1 μs. In a particular embodiment, the nanosystems synthesized have an emission lifetime greater than microsecond for more than 37% of the fluorescence signal In a particular embodiment, the invention relates to a method for determining the authenticity of a security document or article comprising the nanosystems of the invention which comprises:
(a) irradiating the security document or article with one or several external excitation source; and
(b) detecting one or more of the following parameters:
emission wavelength ($\lambda_{em.}$),
intensity,
mean lifetime,
anisotropy,
of said nanosystem by suitable detection means.

The "external excitation source" can be any class of pulsed or continuous intense radiation source, for example light emitting diodes, laser diodes, giant pulse lasers and light sources derived from the same by means of nonlinear optics as well as X-ray pulses or particle beams, particularly pulsed electron beams.

Therefore, in a particular embodiment, the method for determining the authenticity of a security document or article as has been defined previously comprises:
a) irradiating the security document or article with an external radiation source;
b) detecting one or more of the following parameters:
emission wavelength ($\lambda_{em.}$),
intensity,
mean lifetime,
anisotropy,
Of said nanosystem by suitable detection means;
and optionally,
c) comparing the emission wavelength obtained, the intensity, the mean lifetime or the anisotropy obtained in step b) with a value of the emission wavelength, intensity, mean lifetime or reference anisotropy corresponding to a security document or article comprising the luminescent nanosystems.

The authenticity of the security document or article is confirmed in step c) after verifying whether the value of the parameters obtained in step b) coincides with the reference parameters of the security marker, or whether it is within the pre-established limits.

According to another particular embodiment, the emission wavelength, the intensity, the mean lifetime or the anisotropy obtained after impacting the external radiation on the security document or article represents a codification.

Detector

In a particular embodiment, the system for determining the authenticity of a security document, article or element as have been defined previously comprises:
- a positioner wherein the security document, article or element is placed;
- means which allow focusing, transmitting and optionally amplifying the excitation originating from an external excitation source on the part of the document, article or element to be irradiated; and
- detection means suitable for measuring one or more of the following parameters: emission wavelength ($\lambda_{em.}$), intensity, mean lifetime or anisotropy.

In a preferred embodiment the method for detecting the nanosystem additionally comprises in the step for detecting one or more of the following parameters, emission wavelength, $\lambda_{em}$, intensity, mean lifetime or anisotropy, is performed with a particular delayed time. This embodiment is based on the fact that the mean lifetime of the luminescence of the nanosystems of the invention are greater than 0.1 µs. The delayed time for detecting and measuring one or more of the parameters is greater than 0.1 µs and is preferably greater than 1 µs. Thus, possible interferences due to other emission wavelengths, $\lambda_{em}$, which can be created after excitation with an external excitation source at an excitation wavelength, $\lambda_{exc.}$, in addition to the emission wavelength of the nanosystem object of the present invention, are prevented.

"Exciting" is understood in the scope of the present invention as irradiating the nanosystem with a light radiation of a particular wavelength.

The "suitable detection means" relate to methods for detecting and optionally measuring the indicated parameters known by the person skilled in the art, i.e., methods for detecting the emission wavelength of the luminescence, particularly of the fluorescence, methods for detecting the intensity of the luminescence particularly of the fluorescence, methods for detecting the mean lifetime of the intensity of the luminescence or methods for detecting the anisotropy.

In another particular embodiment, this system further comprises a device which allows comparing the parameters obtained with reference parameters and thus verifying if the analyzed document, article or element comprises the security marker.

As used herein, the term "approximately" means a slight variation from the specified value, preferably within 10 percent of the specified value. However, the term "approximately" may mean a greater variation tolerance depending on, for example, the experimental technique used. The person skilled in the art understands said variations of a specified value and they are within the context of the present invention. Furthermore, in order to provide a more precise description, some of the quantitative expressions provided in the present document are not described with the term "approximately". It is understood that, the term "approximately" explicitly used or otherwise, each amount given in the present document attempts to refer to the actual given value, and it also attempts to refer to the approximation of such given value which would be reasonably deduced based on the common knowledge in the art, including equivalents and approximations due to experimental conditions and/or from measurement for such given value.

EXAMPLES

Example 1. Synthesis of Gold AQCs Nanosomes with a Stokes Shift of 300 nm

For this example the method schematically depicted in FIG. 3 was followed.

Figure 4:
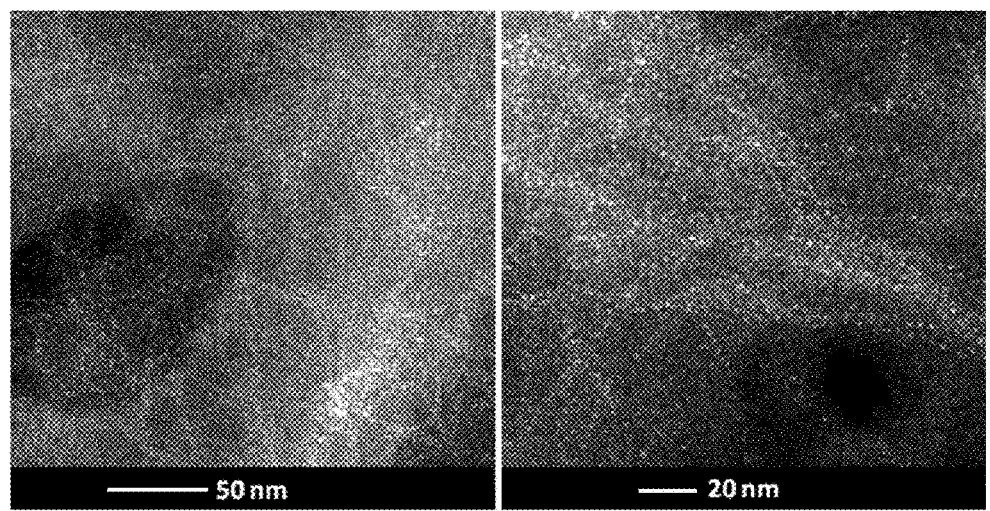
FIG. 4 shows the HAADF STEM electron microscopy images of the nanosystems obtained in Example 1, observing that the approximate size of the nanocavities containing the gold clusters is 1.5 nm.
Figure 5:
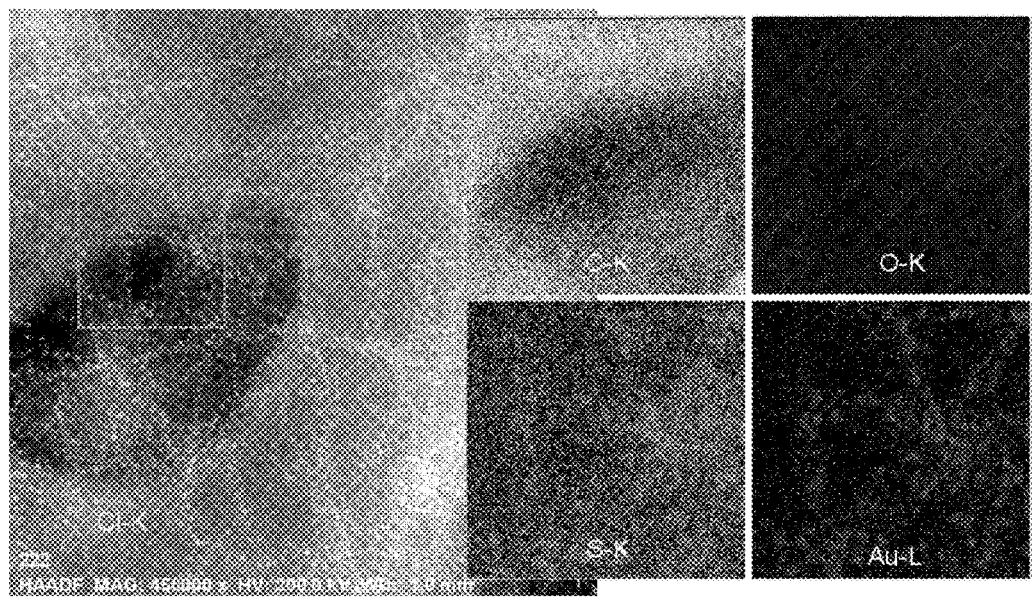
FIG. 5 shows the EDX Map of the images of FIG. 4 showing the composition of the nanosystems, observing that the gold clusters are protected by the molecules forming the nanosomes (C, O, S).
Figure 6:
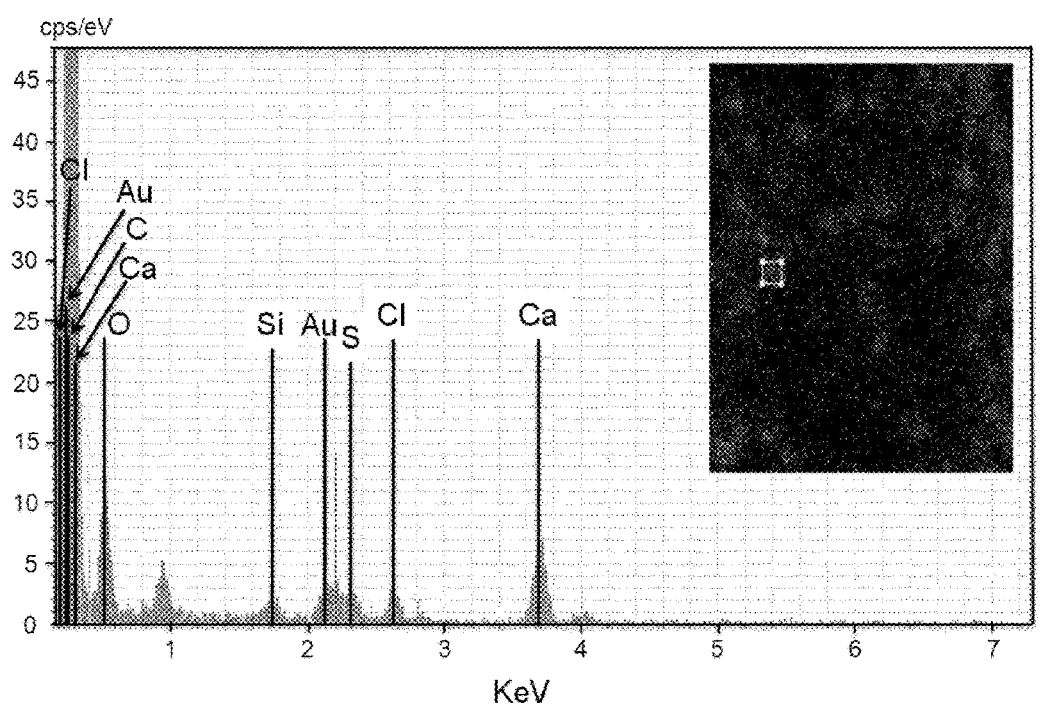
FIG. 6 shows the EDX Spectrum of an individual nanosystem extracted from the map above. The spectrum shows a significant signal of S and O in the region of the nanosystem indicating the presence of molecules containing these atoms (hydroxyl and mercapto acid of nanosome) protecting the Au clusters.
Figure 7:
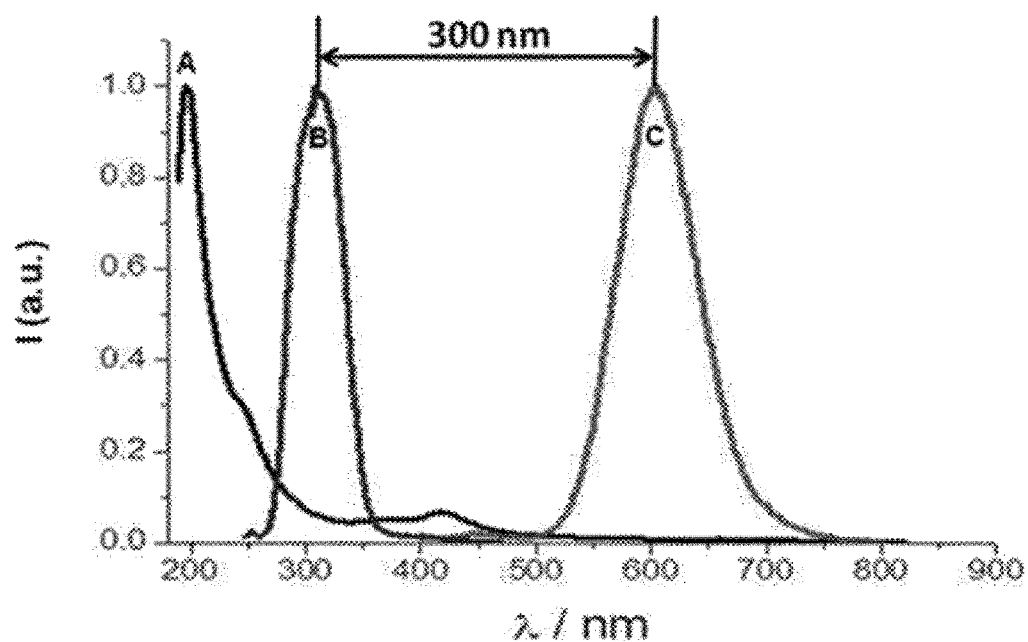
FIG. 7 shows the fluorescence of the nanosystems obtained in Example 1 where A is the absorbance; B is the excitation curve for emission at 600 nm, observing that it maximizes at an excitation wavelength of approximately 300 nm, and C is the emission curve for excitation at 300 nm, observing that it maximizes at a wavelength of approximately 600 nm. The results indicate a Stokes shift of 300 nm. The intensity, I is measured in arbitrary units (a.u.) and the wavelengths ($\lambda$) in nanometers (nm).

An aqueous solution of the 16-hydroxypalmitic acid (2 ml, 10 mg/ml) was mixed with an aqueous solution of 16-mercaptopalmitic acid (0.622 ml, 10 mg/mL) with vigorous stirring in 5.4 ml of water and the necessary volume of tetrabutylammonium hydroxide until producing a basic mean. A volume of 400 µL of $HAuCl_4.3H_2O$ (Au (III) chloride hydrate, metal base at 99.999%, Aldrich) (5.8 mg/ml) solution was added to the resulting solution of nanosomes with subsequent reduction by means of adding 400 µL of a $NaBH_4$ solution (0.05 M). For the concentrations used, the values of R1 and R2 are 3.7 and 3.4, respectively. This gold nanosome stock solution was stirred at 35° C. for 1 hour. In order to purify the nanosomes containing the clusters, it is precipitated by adding acetic acid 0.5 M up to pH 7.8 and centrifuged to separate the solid containing excess reagents and nanosomes from the supernatant which contains the nanosomes with clusters. Finally, this supernatant is filtered through a filter of 0.45 microns. An electronic microscopy image STEM (scanning transmission electron microscopy) obtained by means of a Tecnai OSIRIS microscope equipped with HAADF (high angular annular dark field) and EDX (energy-dispersive X-ray spectroscopy) detectors, of the Au AQC nanosome samples obtained in the present example is shown in FIG. 4, it is observed that the approximate size of the nanocavities of the nanosomes containing the AQCs is approximately 1.5 nm. FIG. 5 shows the chemical analysis of FIG. 4 by means of EDX, it is observed that the Au clusters are protected by the molecules forming the nanosomes (C, O, S). FIG. 6 shows the EDX result of the typical analysis of one of the individual nanosomes observed in FIG. 4. The spectrum shows a significant S and O signal of in the region of the nanosystem which indicates the presence of molecules containing these atoms (hydroxyl and mercapto acid of the nanosome) protecting the Au clusters. Images of HR-STEM (high resolution) obtained with the same piece of equipment in turn show the complete absence of crystallinity characteristic of the presence of Au in the form of clusters (AQCs). FIG. 7 shows the absorption spectrum (measured with a Hewlett-Packard HP8452A spectrophotometer in a quartz cuvette of 1 mm×1 cm×3 cm), excitation spectrum and emission spectrum (measured with a Cary Eclipse Varian fluorescence spectrophotometer) of the Au AQC nanosomes, observing that they present maximum excitation at 300 nm and maximum emission at 600 nm which indicates a Stokes shift of 300 nm. The excitation at 300 nm in turn indicates, according to Table 1, that the excitation donor clusters present in the nanosomes have between 3 and 5 atoms, meanwhile the emission acceptor clusters have about 15 atoms.

Example 2 Synthesis of Au AQCs Nanosomes with a Stokes Shift of 370 nm

Figure 8:
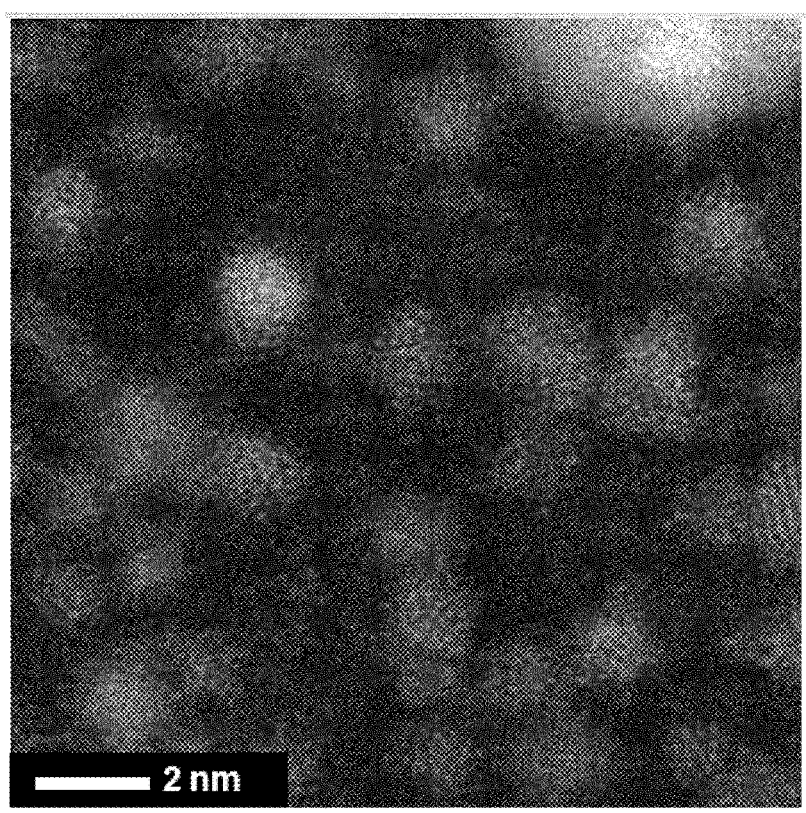
FIG. 8 shows the HAADF STEM electron microscopy images of the gold nanosystems obtained in Example 2. It is observed that the approximate inner diameter of the nanocavities containing the clusters is approximately 1.8 nm. Individual atoms of the clusters can also be observed inside the cavity.
Figure 9:
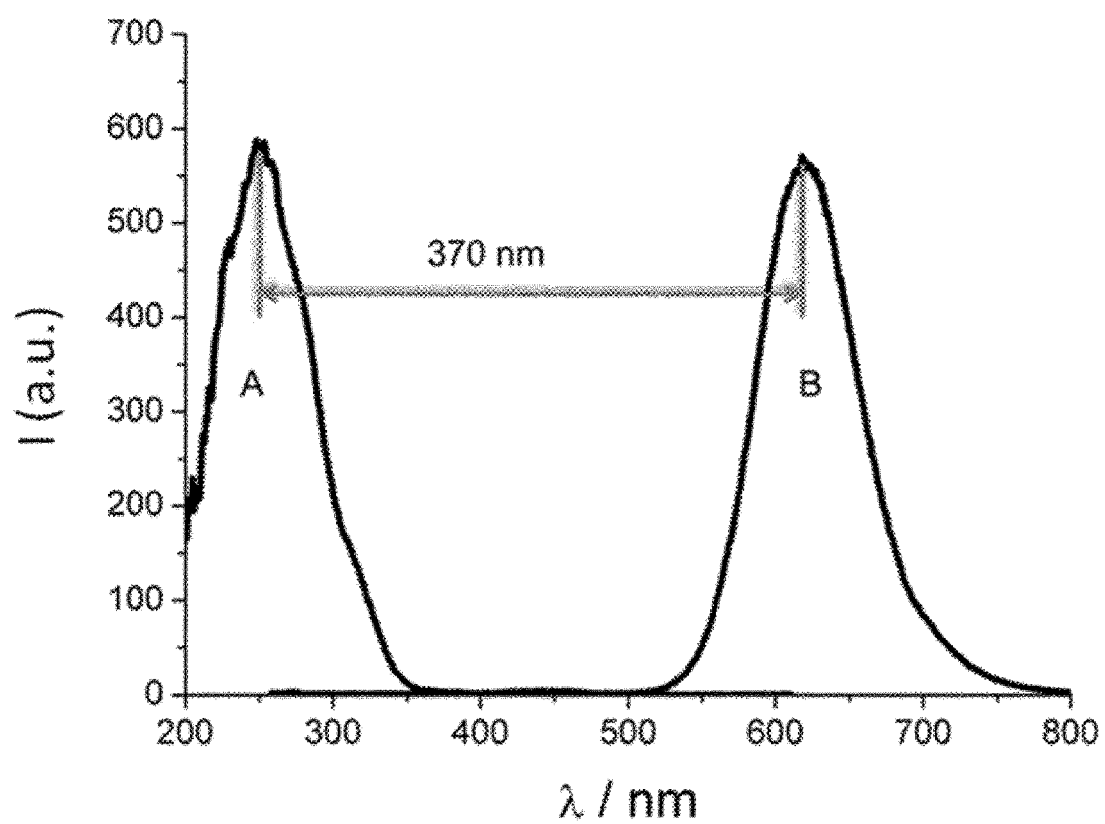
FIG. 9 shows the fluorescence of the nanosystems obtained in Example 2 where A represents the excitation curve for emission at 620 nm, observing that it maximizes at a excitation wavelength of approximately 250 nm, and B is the emission curve for excitation at 250 nm, observing that it maximizes at a wavelength of approximately 620 nm. The results indicate a Stokes shift of 370 nm. The intensity, I is measured in arbitrary units (a.u.) and the wavelengths ($\lambda$) in nanometers (nm).

In order to achieve a Stokes shift greater than that described in Example 1, it is necessary to reduce the size of the acceptor clusters and to increase that of the donors. As described in the specification this is achieved by increasing the values of R1 and R2 with respect to the values used in Example 1. The selected values in this example were R1=4.1 and R2=4.3. It then proceeded in the following manner. An aqueous solution of 16-hydroxypalmitic acid (2.52 ml, 10 mg/mL) was mixed with the aqueous solution of 16-mercaptopalmitic acid (0.622 ml, 10 mg/mL) with vigorous stirring in 4.9 ml of water and the necessary volume 5 of tetrabutylammonium hydroxide until neutralization. A volume of 360 μL of a solution of $HAuCl_4 \cdot 3H_2O$ (Au (III) chloride hydrate, metal base at 99.999%, Aldrich) (5.8 mg/ml) was added to the resulting solution of nanosomes with subsequent reduction by means of adding 400 μL of a $NaBH_4$ solution (0.05 M). This gold nanosome stock solution was stirred at 25° C. for 30 minutes. In order to purify the nanosomes containing the clusters, they are precipitated by adding acetic acid 0.5 M up to pH 7.8 and centrifuged to separate the solid containing the excess reagents and nanosomes from the supernatant which contains the nanosomes with clusters. Finally, this supernatant is filtered through a filter of 0.45 microns. FIG. 8 shows a high resolution HAADF-STEM image obtained by means of a Jeol JEM-ARM200F microscope equipped with spherical aberration correction where the Au clusters of approximate size of 1.8 nm occupying the cavities of the nanosomes can be clearly seen. The image allows visualizing the atoms forming the clusters enclosed inside the nanocavities of the nanosomes. FIG. 9 shows the excitation and emission spectra (measured with a Cary Eclipse Varian fluorescence spectrophotometer) of the Au AQC nanosomes, observing that they present maximum excitation at 250 nm and the maximum emission at 620 nm which indicates a Stokes shift of 370 nm. The position of the maximum excitation and emission in turn indicates, according to Table 1, that the donor Au clusters present in the nanosomes have between 2 and 3 atoms, meanwhile the emission acceptor clusters have about 20 atoms.

Example 3. Synthesis of Ag AQCs Nanosomes

Firstly, stock solutions of 16-mercaptopalmitic acid and 16-hydroxypalmitic acid are prepared at a concentration of 10 mg/ml, a given volume of tetrabutyl ammonium hydroxide solution (1.5 M in water) is added to ensure a molar ratio of fatty acid/TBAOH of 1. Then nanosomes are prepared mixing a given volume of each fatty acid stock solution with 25 ml of pure water (3.11 ml of 16-mercaptohexadecanoic acid and 10 ml of 16-hydroxyhexadecanoic acid).

In a second step, a stock solution of 0.0147 M $AgNO_3$ is prepared in pure water. Then 2.7 ml of this solution is poured in the nanosome sample. An extra amount of TBAOH solution is added to the mixture to ensure redispersion of the material. Then, 2.7 ml of a freshly prepared stock solution of 0.05 M $NaBH_4$ is added to the sample dropwise under vigorous agitation. The reaction is finished after 1 hour stirring at 35° C. in a thermostatted bath.

Example 4. Synthesis of Au AQCs Short-Chain-Length Nanosomes

Firstly, stock solutions of 12-mercaptododecanoic acid and 12-hydroxydodecanoic acid are prepared at a concentration of 10 mg/ml, a given volume of tetrabutyl ammonium hydroxide (TBAOH) solution (1.5 M in water) is added to ensure a molar ratio of fatty acid/TBAOH of 1. Then nanosomes are prepared mixing a given volume of each fatty acid stock solution with 25 ml of pure water (3.11 ml of 12-mercaptododecanoic acid and 10 ml of 12-hydroxydodecanoic acid).

In a second step, a stock solution of 0.0147 M $HAuCl_4$ is prepared in pure water. Then 2.7 ml of this solution is poured in the nanosome sample. An extra amount of TBAOH solution is added to the mixture to ensure redispersion of the material. Then, 2.7 ml of a freshly prepared stock solution of 0.05 M $NaBH_4$ is added to the sample dropwise under vigorous agitation. The reaction is finished after 1 hour stirring at 35° C. in a thermostatted bath.

Example 5. Synthesis of Au AQCs Encapsulated by Inverse Micelles (Microemulsions)

Gold cluster encapsulated by inverse micelles (microemulsions) are prepared by mixing two different previous prepared microemulsions: one containing a $HAuCl_4$ salt and the other one containing $NaBH_4$.

The first microemulsion is prepared by dissolving 15.4 ml of Tergitol® 15S5, 1.37 ml of 1-butanethiol and 2.7 ml of an aqueous solution of $HAuCl_4$ (0.0147 M) in 80.6 ml of isooctane. The second microemulsion is prepared by dissolving 15.4 ml of Tergitol® 15S5, 1.37 ml of 1-butanethiol and 2.7 ml of an aqueous solution of $NaBH_4$ (0.05 M) in 80.6 ml of isooctane.

Then, both microemulsions are mixed and the reaction is stirred during 24 h.

Example 6—Use of Nanosystems of Two Au Clusters of 3-5 and 20-25 Atoms Encapsulated in Nanosomes as Security Markers Applied on the Surface in Security Paper for Printing Legal Tender Notes This example uses a gravure printing machine manufactured by Panday-Graph, a gravure cylinder manufactured by Ziraba, natural cellular-based fibrous paper manufactured in a round paper machine in the Fábrica Nacional de Moneda y Timbre (FNMT), long-lasting varnish and crosslinker manufactured by Sicpa and a aqueous solution of Au clusters encapsulated in nanosomes.

The main characteristics of the installations and materials indicated are described below:
Conditions of the printing machine on each side of the paper:
  Drying tunnel temperature: 145° C.
  Machine speed: 90 m/min
  Suction speed: 2500 rpm
  Blowing speed: 2400 rpm
  Residual moisture of the paper after drying: 6.1-6.8%
Conditions of the gravure cylinder
  Type of etching: chemical
  Lineature: 60 line/cm
  Cell depth: 54 microns
  Table: 910 mm
  Diameter: 200 mm
Conditions of the varnish and crosslinker:
  Commercial name of the varnish: Primer 803696W
  Commercial name of the crosslinker: First additive 370010
  Viscosity of the varnish after adding crosslinker: 20 s CP4
  Viscosity of the varnish for application: 18 s CP4
Main conditions of the paper:
  Fibrous composition: 100% cellulose
  Grammage: 90 g/m$^2$
  Grammage after the varnishing process: 96 g/m$^2$
  Thickness: 115 microns Bendtsen smoothness on the felt side: <700 ml/min
Bendtsen smoothness on the fabric side: <800 ml/min
Bendtsen porosity: <20 ml/min
Bendtsen porosity after creasing: <140 ml/min
Cobb value: 40-70 g/cm$^2$
Ash: <3%
Opacity: 84%

Implementation Method:

Once the printing machine is started up to reach the established machine conditions, the gravure cylinder is placed, the reel of paper is placed on the unwinding screw and the web of paper is distributed in the machine circuit, the varnish is mixed with the crosslinker in a proportion of 1.5% by weight of the latter over the former, under gentle stirring conditions in the actual 20 kg drum of varnish. 100 ml of the aqueous solution of Au clusters encapsulated in nanosomes are added to this mixture. Once the perfect dispersion of the components is assured, the content of the drum is pumped to the inkwell of the printing machine. The paper is positioned on the printing cylinder starting the application of the varnish on the entire width of the web of paper on one of the sides, controlling the final moisture of the paper, viscosity of the varnish and the machine conditions throughout the entire printing process. Once the paper is wound at the machine outlet, the reel is taken off the winder and is placed in the unwinder in the appropriate unwinding direction to print the varnish on the opposite side. After the process ends the reel is left at rest for a minimum development time of 24 hours at room temperature (23° C. and 50% RH).

Example 7—Use of Nanosystems of Two Au Clusters of 2-10 and 25-50 Atoms Respectively Encapsulated in a Reverse Micelle as Security Markers Applied in Security Paper Mass Intended for Printing Passports This example uses a round paper machine and an aqueous dispersion of cellulose fibers suitably bleached and refined in previous production processes along with different chemical products such as anti-foaming agents, charge retention agents, color fixing agents, mineral fillers such as titanium dioxide or alumina silicate, pigment dyes, ion and pH regulators and dry resistance resins such as carboxymethyl cellulose (all of them being added in specific amounts depending on the characteristics of the paper to be manufactured which amounts are not mentioned as they are not relevant to the properties to be achieved with the security markers), form the base pulp for manufacturing paper with a consistency or concentration around 3% by weight with respect to the amount of water used with pH between 7 and 8.

The Au clusters encapsulated in reverse micelles functionalized to be cationic and to have the capacity to form covalent bonds with the oxygen atoms of the carboxyl groups of the cellulose fibers is also in an aqueous dispersion in a 1000 kg dilution tank.

The metering of the Au clusters encapsulated in reverse micelles towards the machine head vat first causes an electrostatic attraction between the reverse micelles and the anionic fibers to later form the indicated covalent bond.

Wet resistance resin based on polyamide-epichlorohydrin which is also strongly cationic and has the possibility of forming covalent bonds similar to that indicated is subsequently added to the paper pulp, and such bonds are formed with as many cellulose fibers are left with this option and it also forms such bonds with itself to form the polymer lattice necessary to render the paper with the specified wet resistance level.

This entire mass of cellulose fibers and chemical additives subsequently arrive from the machine head ink to the round shape where the layer of paper forming the final sheet of paper after the pressing, drying, gluing and subsequent drying and calendering processes is formed.

The paper manufactured by these means is subsequently used for printing passports.

Example 8—Use of Nanosystems of Two Au Clusters of 3-5 and 20-25 Atoms Encapsulated in Nanosomes as Security Markers Applied in Silk-Screen Printing Ink with an Iridescent Web in Security Paper for Security Labels This example uses a silk-screen printing machine manufactured by Stork, a silk screen manufactured by Stork, natural cellular-based fibrous paper manufactured in a round paper machine in the FNMT, iridescent ink, anti-foaming agent and crosslinker manufactured by Sicpa and a dispersion of fluorescent AQC aqueous solution of Au clusters encapsulated in nanosomes.

The main characteristics of the installations and materials indicated are described below:

Conditions of the printing machine on each side of the paper:
　Drying tunnel temperature: 145° C.
　Machine speed: 70 m/min
　Suction speed: 2500 rpm
　Blowing speed: 2400 rpm
　Residual moisture of the paper after drying: 6.5%

Conditions of the silk screen
　Reference: RSI900
　Development: 25⅜"
　Mesh: 105
　Open area: 15%
　Thickness: 105 microns
　Width: 910 mm Conditions of the iridescent ink and additives:
　Commercial name of the ink: Silk-screen printing ink 5WR1241
　Commercial name of the anti-foaming agent: Additive 880775
　Commercial name of the crosslinker: Additive 370010
　Viscosity of the ink after adding crosslinker: 20 s CP4
　Viscosity of the printing ink: 18 s CP4

Main conditions of the paper:
　Fibrous composition: 100% cotton cellulose
　Grammage: 90 g/m$^2$
　Grammage after the varnishing process: 96 g/m$^2$
　Thickness: 115 microns
　Bendtsen smoothness on the felt side: <700 ml/min
　Bendtsen smoothness on the fabric side: <800 ml/min
　Bendtsen porosity: <20 ml/min
　Bendtsen porosity after creasing: <140 ml/min
　Cobb value: 40-70 g/cm$^2$
　Ash: <3%
　Opacity: 84%

Implementation Method:

Once the printing machine is started up to reach the established machine conditions, the silk screen is placed, the reel of paper is placed on the unwinding screw and the web of paper is distributed in the machine circuit, the ink is mixed with the crosslinker in a proportion of 1.5% by weight of the latter over the former, under gentle stirring conditions in the actual 20 kg drum of ink. 100 ml of the aqueous solution of Au clusters encapsulated in nanosomes and anti-foaming agent are added to this mixture as needed should foam occur. Once the perfect dispersion of the components is assured, the content of the drum is pumped to the inkwell of the printing machine. The paper is positioned on the printing silk screen starting the printing of the ink through the holes of the screen according to the graphic design established therein on one of the sides, controlling the final moisture of the paper, viscosity of the ink and the machine conditions throughout the entire printing process.

Example 9—Use of Nanosystems of Two Ag Clusters of 2-8 and 15-30 Atoms Encapsulated in Nanosomes as Security Markers Applied on the Surface of the Security Paper Intended for Printing Passports This example uses a round paper machine and an aqueous dispersion of cellulose fibers suitably bleached and refined in previous production processes along with different chemical products such as anti-foaming agents, charge retention agents, color fixing agents, mineral fillers such as titanium dioxide or alumina silicate, pigment dyes, ion and pH regulators and dry resistance resins such as carboxymethyl cellulose (all of them being added in specific amounts depending on the characteristics of the paper to be manufactured which amounts are not mentioned as they are not relevant to the properties to be achieved with the security markers), form the base pulp for manufacturing paper with a consistency or concentration around 3% by weight with respect to the amount of water used with pH between 7 and 8.

Wet resistance resin based on polyamide-epichlorohydrin which is also strongly cationic and has the possibility of forming covalent bonds similar to that indicated is subsequently added to the paper pulp, and such bonds are formed with as many cellulose fibers are left with this option and it also forms such bonds with itself to form the polymer lattice necessary to render the paper with the specified wet resistance level.

This entire mass of cellulose fibers and chemical additives subsequently arrive from the machine head ink to the round shape where the layer of paper is formed after the pressing and drying processes.

After drying, the paper will move to the gluing area where it will be immersed in a tray that will contain a dilution of gluing agents based on polyvinyl alcohol (reference Airvol 103 manufactured by Air Products & Chemical) where 100 ml of aqueous solution of Ag clusters encapsulated in nanosomes suitably functionalized to have the capacity to form covalent bonds with the oxygen atoms of the hydroxyl groups of the gluing agent will have been added for every 100 liters of gluing agent.

The paper is subsequently dried and calendered until obtaining absolute moisture of the paper of 5%.

The paper manufactured by these means is subsequently used for printing passports.

Example 10—Use of Nanosystems of Two Au Clusters of 3-5 and 20-25 Atoms Encapsulated in Nanosomes as Security Markers Applied in the Coated Layer of Paper Intended for Printing Self Adhesive Security Labels This example uses a knife coating machine which is supplied with a coating slip previously prepared according to the following specially indicated formula for the use of the coated paper in offset printing techniques for self-adhesive security labels.

Mineral fillers: 80% calcium carbonate (Ref Albacar HO Slurry manufactured by Specialty Minerals) and 20% kaolin (reference Supragloss 95 manufactured by Imerys) to obtain 50 parts of the slip.
Synthetic binder: 10 parts butadiene styrene latex (reference Styronal D-517 manufactured by BASF).
Synthetic co-binder: 2 parts (reference Acronal 700 L manufactured by BASF).
Thickener: 1 part carboxymethyl cellulose.
Insolubilizing agent: 1 part (reference Basocoll OV manufactured by BASF).
Additives: 1 part sodium hydroxide.
Aqueous solution of Au clusters encapsulated in nanosomes: 1 part.
Water: The rest up to 100 parts.
The self-adhesive paper to be coated has the following characteristics:
  Total grammage: 200 g/m$^2$
  Grammage of siliconized support: 82 g/m$^2$
  Grammage of adhesive: 20 g/m$^2$
  Fibrous composition of the front side: 100% cellulose from mechanical pulp
Conditions of the coating machine:
  Drying tunnel temperature: 145° C.
  Machine speed: 150 m/min
  Residual moisture of the paper after drying: 6.5%
Characteristics of the coated paper:
  Total grammage: 220 g/m$^2$
  Grammage of coated layer: 20 g/m$^2$
  Bekk smoothness on the coated side: 200 sec
  Ash: 20%
  Opacity: 84%
Implementation Method:
Once the coating machine is started up to reach the established machine conditions, the reel of paper is placed on the unwinding screw and the web of paper is distributed in the machine circuit, the coating slip is metered into the tray of the knife coater and the coating process begins according to the established machine conditions until finishing the reel.

After the coating process, the reel of paper is calendered until reaching the smoothness established and is cut to the format necessary for the subsequent process of sheet or reel printing of the security labels.

Example 11—Use of Nanosystems of Two Au Clusters of 2-5 and 10-20 Atoms Encapsulated in Short-Chain Nanosomes as Security Markers Applied in the Security Fiber Mass Intended for Inclusion in Security Paper Mass This example uses a plastic material extrusion machine made up of a metering hopper with circular section where the chips of polymer material will be metered, a piston meter where the Au clusters encapsulated in short-chain nanosomes will be metered, a single screw extruder with Maddock type mixer and spinning head, an air cooling system, a fiber tempering or tensing system and a cutter. The main process parameters in use and the configuration parameters of this machine are indicated below.

Configuration of the screw of the extruder:
  Screw diameter: 5 cm
  Screw length in the feeding area: 50 cm
  Screw length in the compression area: 30 cm Screw length in the metering area: 20 cm
Angle of the blades: 17.65°
Thread pitch: 5 cm
Gap between cylinder and screw: 0.5 cm
Depth of the metering channel; 0.25 cm
Depth of feeding channel 0.75 cm
Outer diameter of the cylinder: 7.01 cm
Inner diameter of the cylinder: 5.01 cm
Length of the mixer: 10 cm
Number of holes of the spinning head: 50
Diameter of the holes: 0.15 mm
Process parameters of the extruder:
Range of temperatures along the cylinder: 120-185°
Fiber flow rate at the outlet of the spinning head: 10 l/h
Output speed: 3.14 m/s (7.5 kg of fiber/hour)
Characteristics of the polymer material:
Composition: polypropylene manufactured by LyonDell-Basell (ref.: HM560R)
Chip density: 0.91 g/cm$^3$
Melting temperature: 145° C.
Fluidity Index: 25 g/10 min (230° C./2.16 kg)
Characteristics of the security fibers:
Thickness: 0.02 mm
Length 3 mm
Implementation Method:

Once the extrusion machine is started up in the indicated configuration and process parameters, coat to reach the established machine conditions, the heated hopper is fed with the polypropylene chips. The markers with Au clusters encapsulated in short chain nanosomes will be introduced by using a vertical piston meter located between the feeding area and the compression area of the extruder. The material is gradually mixed and pressed as it moves along the screw starting with an atmospheric pressure in the hopper and increasing until the outlet through the nozzle. Before reaching the mixer, the components pass through a mesh or filter. After going through the mixer the material is subjected to maximum pressure and passes through a spinning head provided with small holes where the fibers will be produced.

Once the fibers are obtained, they must be cooled by means of an air current and are subsequently collected by a drive roller feeding the tensing unit. In this unit the fibers align their crystalline structure in the direction of the axis of the filament enabling their lengthening which will be produced through the action of a roller which is at the end of the drying chamber and which rotates at a speed 4 times faster than that of the outlet of the spinning head.

Then another roller will drive the fibers to the cutting machine where a set of stationary blades will cut the fibers into the specific length.

Example 12—Use of Nanosystems of Two Au Clusters of 3-5 and 20-25 Atoms Encapsulated in Nanosomes as Security Markers Applied in Silk-Screen Printing Ink of Polymeric Substrates for Identification Cards This example use a silk-screen printing machine jointly manufactured by Stork and Thieme with ultraviolet drying, a Rotaplate silk screen manufactured by Stork, polyester-based polymeric substrate, silk-screen printing ink manufactured by Sicpa and a aqueous solution of Au clusters encapsulated in nanosomes.

The main characteristics of the installations and materials indicated are described below:

Conditions of the printing machine on each side of the paper:
Machine speed: 4000 sheets/hour
Conditions of drying: 60%
Conditions of the silk screen Rotaplate 125W
Mesh: 125 hpi
Thickness: 120 microns
Open area: 43%
Diameter: 140 microns
Conditions of the iridescent ink and additives:
Commercial name of the ink: Silk-screen printing ink 3Z1Q09
Viscosity of the printing ink: 120 s CP4
Main conditions of the polymeric substrate:
Composition: polyester manufactured by PPG Industries (Ref.: Teslin SP 1000)
Thickness: 200 microns
Implementation Method:

Once the printing machine is started up to reach the established machine conditions, the silk screen is placed and those of polyester are positioned, a mixture of silk-screen printing ink to which 100 ml of the aqueous solution of Au clusters encapsulated in nanosomes will have been previously added will be pumped to the inkwell. The printing of the ink through the holes of the screen according to the graphic design established therein on one of the sides, controlling the viscosity of the ink and the machine conditions throughout the entire printing process is subsequently started.

Example 13—Use of Nanosystems of Two Ag Clusters of 2-8 and 15-30 Atoms Encapsulated in Nanosomes as Security Markers Applied in the Coated Layer of Paper Intended for Printing Postal Mail Stamps This example uses a filmpress coating machine which is supplied with a coating slip previously prepared according to the following formula such that the type and characteristics of the coating obtained is specially indicated for a use of the coated paper in gravure printing techniques for postal mail stamps
Mineral fillers: 50 parts kaolin (reference Supragloss 95 manufactured by Imerys).
Synthetic binder: 12 parts butadiene styrene latex (reference L-8000 manufactured by EOC Polymers).
Synthetic co-binder: 2 parts (reference Acronal 700 L manufactured by BASF).
Thickener: 1 part of carboxymethyl cellulose.
Insolubilizing agent: 1 part (reference Basocoll OV manufactured by BASF).
Additives: 1 part sodium hydroxide.
Aqueous solution of Ag clusters encapsulated in nanosomes: 1 part.
Water: The rest up to 100 parts.
The support paper to be coated has the following characteristics:
Total grammage: 90 g/m$^2$
Thickness: 120 microns
Fibrous composition: 100% cellulose from mechanical pulp
Conditions of the coating machine:
Drying tunnel temperature: 150° C.
Machine speed: 170 m/min
Residual moisture of the paper after drying: 5.5%
Characteristics of the coated paper:
Total grammage: 110 g/m$^2$
Grammage of coated layer: 20 g/m$^2$ Bekk smoothness on the coated side: 1800 sec Ash: 15%

Opacity: 80%

Implementation Method:

Once the coating machine is started up to reach the established machine conditions, the reel of paper is placed on the unwinding screw and the web of paper is distributed in the machine circuit, the coating slip is metered into the tray for supplying the cylinders in contact with the paper and the coating process begins according to the established machine conditions until finishing the reel.

After the coating process, the reel of paper is calendered until reaching the established smoothness and is cut to the format necessary for the subsequent process for sheet or reel printing of postal mail stamps.

Example 14—Use of Nanosystems of Two Au Clusters of 3-5 and 20-25 Atoms Encapsulated in Nanosomes as Security Markers Applied in the Gummed Layer of Paper Intended for Printing Gummed Tax Stamps or Security Labels This example uses a filmpress coating machine which is supplied with a slip of previously conditioned re-wettable gum which is specially indicated for the use of gummed paper for offset printing techniques for gummed tax stamps or security labels.

The slip of re-wettable gum used is based on polyvinyl acetate, reference A-4524 manufactured by Henkel Adhesives & Technologies. 1 liter of aqueous dispersion of Au clusters encapsulated in nanosomes and 1400 grams of green food dye with reference Verde Carta DAM Liquido manufactured by Clariant previously prepared by mixing 1 part of the dye indicated with 3 parts water are added for every 1000 kg tank of gum slip The support paper to be gummed has the following characteristics:

Total grammage: 95 g/m$^2$

Thickness: 98 microns

Fibrous composition: 100% cellulose from mechanical pulp

Conditions of the coating machine:

Drying tunnel temperature: 130° C.

Machine speed: 140 m/min

Residual moisture of the paper after drying: 5.5%

Characteristics of the gummed paper:

Total grammage: 105 g/m$^2$

Grammage of coated layer: 10 g/m$^2$

Re-wettable gum adhesion: 25 gF/mm

Ash: 10%

Opacity: 80%

Implementation Method:

Once the coating machine used to apply the re-wettable gum is started up to reach the established machine conditions, the reel of paper is placed on the unwinding screw and the web of paper is distributed in the machine circuit, the gum slip is metered into the tray for feeding the cylinders in contact with the paper and the gumming process begins according to the established machine conditions until finishing the reel.

After the gumming process, the reel of paper is cut to the format necessary for the subsequent process for sheet or reel printing of the gummed tax stamps or security labels.

Example 15—Use of Nanosystems of Two Au Clusters of 3-5 and 20-25 Atoms Encapsulated in Nanosomes as Security Markers Applied on the Surface in Cellulose Tapes for Insertion into the Security Paper Mass Intended for Printing Legal Tender Notes This example uses a gravure printing machine manufactured by Giave, a gravure cylinder manufactured by Artcyl and etched by Ziraba, natural cellular-based fibrous paper manufactured by Miguel and Costas, gravure ink manufactured by Sicpa and a aqueous solution of Au clusters encapsulated in nanosomes.

The main characteristics of the installations and materials indicated are described below:

Conditions of the printing machine on each side of the paper:

Drying tunnel temperature: 45° C.

Machine speed: 80 m/min

Reel tension: 150 N

Heliofun (antistatic system): 60%

Conditions of the gravure cylinder

Type of etching: chemical

Lineature: 90 line/cm

Cell depth: 34 microns

Table: 510 mm

Diameter: 24"=194.02 mm

Conditions of the ink:

Commercial name of the ink: 67E9011

Viscosity of the ink: 32 s CP4

Viscosity of the varnish for application: 32 s CP4

Main conditions of the paper:

Fibrous composition: 100% cellulose

Grammage: 18 g/m$^2$

Thickness: 30 microns

Bendtsen porosity: 144 ml/min

Opacity: 25%

Implementation Method:

Once the printing machine is started up to reach the machine conditions, the gravure cylinder is placed on the unwinding screw and the web of paper is distributed in the machine circuit the ink is mixed with 100 ml of the aqueous solution of Au clusters encapsulated in nanosomes. Once the perfect dispersion of the components is assured, the content of the drum is pumped to the inkwell of the printing machine. The paper is positioned on the printing cylinder starting the printing of the ink on the paper on one of the sides, controlling the final moisture of the paper, viscosity of the ink and the machine conditions throughout the entire printing process. After the process ends the reel is left at rest for a minimum development time of 24 hours at room temperature (23° C. and 50% RH).

The invention claimed is:

1. A method of marking a document, article, or element for security enhancement thereof, said method comprising incorporating in said document, article, or element, a nanosystem comprising metal atomic quantum clusters (AQCs) of at least two different sizes encapsulated in a cavity with an inner diameter less than or equal to approximately 10 nm, as a marker for said document, article or element.

2. The method according to claim 1, wherein said nanosystem is formed by a nanosome, micelle, or a reverse micelle, and wherein the cavity is the core of said nanosystem.

3. The method according to claim 1, wherein the cavity is the core of a nanosome, and wherein the nanosome comprises ω-hydroxyacids and ω-mercaptoacids.

4. The method according to claim 1, wherein the metal AQCs are made up of metal atoms, in a range selected from the group of ranges consisting of: (i) between 2 and 309 metal atoms ($M_n$, $2 \leq n \leq 309$), (ii) between 2 and 102 metal atoms ($M_n$, $2 \leq n \leq 102$), (iii) between 2 and 55 metal atoms ($M_n$, $2 \leq n \leq 55$) and (iv) between 2 and 25 metal atoms ($M_n$, $2 \leq n \leq 25$).

5. The method according to claim 1, wherein the atom difference between the AQCs of at least two different sizes is at least three atoms.

6. The method according to claim 1, wherein the metals of the AQCs are transition metals or the combinations thereof.

7. The method according to claim 1, wherein after exciting the nanosystem by an external excitation source luminescence, preferably fluorescence, is produced in the nanosystem.

8. The method according to claim 1, wherein the Stokes shift is greater than approximately 150 nm.

9. The method according to claim 1, wherein the fluorescent nanosystem has a decaying time greater than 0.1 microsecond.

10. A security element, security article or security document, comprising an element, article or document incorporating a nanosystem comprising metal atomic quantum clusters (AQCs) of at least two different sizes encapsulated in a cavity with an inner diameter less than or equal to approximately 10 nm.

11. An element according to claim 10 selected from substrate body, security threads, security fibers, watermarks, tactile effects, security cellulose strips, layers of glues, lacquers, plasters, planchettes, holograms, security inks and plastic sheets.

12. A document or article according to claim 10, selected from security paper, envelopes, cheques, bank notes, identity documents, tickets, stamps, admission passes, impressed and certified papers.

13. A method of manufacturing an element, document or article, comprising incorporating therein a nanosystem comprising metal atomic quantum clusters (AQCs) of at least two different sizes encapsulated in a cavity with an inner diameter less than or equal to approximately 10 nm,
 i) during the manufacturing of material used to manufacture the document or article,
 ii) as part of an additive which is added to the element, document or article,
 iii) on the surface of said article or document, or
 iv) as part of one or more of dyes or inks used in manufacturing of the document or article.

14. A method for determining the authenticity of a document, article or element as defined in claim 10, which comprises:
 (a) irradiating the document, article or element with an external excitation source at a pre-determined excitation wavelength, $\lambda_{exc.}$ to excite the nanosystem, and
 (b) detecting one or more of the following parameters:
  emission wavelength ($\lambda_{em.}$),
  intensity,
  mean lifetime, and
  anisotropy,
  of said nanosystem.

15. A system for determining the authenticity of a document, article or element according to claim 10, comprising:
 a positioner wherein the security document, article or element is placed;
 a radiation assembly adapted to focus, transmit, and optionally amplify excitation radiation originating from an external excitation source on a part of the document, article or element; and
 a detector adapted for measuring one or more of the following parameters: emission wavelength ($\lambda_{em.}$), intensity, mean lifetime or anisotropy.

16. The method according to claim 6, wherein the metals of the AQCs are selected from Au, Ag, Co, Cu, Pt, Fe, Cr, Pd, Ni, Rh and combinations thereof.

17. The method according to claim 7, wherein the external excitation source luminescence comprises fluorescence.

18. The method according to claim 8, wherein the Stokes shift is greater than approximately 300 nm.

19. The method according to claim 9, wherein the fluorescent nanosystem has a decaying time greater than one microsecond.

20. A security element as marker for security articles or documents comprising a nanosystem comprising metal atomic quantum clusters (AQCs) of at least two different sizes encapsulated in a cavity with an inner diameter less than or equal to approximately 10 nm, wherein said security element is selected from the group consisting of substrate body, security threads, security fibers, watermarks, tactile effects, security cellulose strips, layers of glues, lacquers, plasters, planchettes, holograms, security inks and plastic sheets.

21. A marker on a security element, said marker comprising a nanosystem comprising metal atomic quantum clusters (AQCs) of at least two different sizes encapsulated in a cavity with an inner diameter less than or equal to approximately 10 nm, wherein said security element is selected from the group consisting of substrate body, security threads, security fibers, watermarks, tactile effects, security cellulose strips, layers of glues, lacquers, plasters, planchettes, holograms, security inks and plastic sheets.

22. An article comprising a nanosystem comprising metal atomic quantum clusters (AQCs) of at least two different sizes encapsulated in a cavity with an inner diameter less than or equal to approximately 10 nm, wherein said article is selected from the group consisting of substrate body, security threads, security fibers, watermarks, tactile effects, security cellulose strips, layers of glues, lacquers, plasters, planchettes, holograms, security inks and plastic sheets.

23. A nanosystem comprising metal AQCs of at least two different sizes encapsulated in a cavity with an inner diameter less than or equal to 10 nm, wherein the metal of the metal AQCs is (i) a transition metal selected from the group consisting of scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, mercury, rutherfordium, dubnium, seaborgium, bohrium, hassium, meitnerium, damstadtium, roentgenium, and copernicium, or (ii) a combination of transition metals.

24. The nanosystem according to claim 23, wherein the transition metal is Ag or Cu.

25. The nanosystem according to claim 23, wherein the cavity is the inner cavity of a nanosome comprising hydroxyacids and mercaptoacids, and wherein the metal AQCs of at least two different sizes are characterized by being made up of: between 2 and 309 metal atoms (Mn, 2<n<309), between 2 and 102 metal atoms (Mn, 2<n<102), between 2 and 55 metal atoms (Mn, 2<n<55), and or between 2 and 25 metal atoms (Mn, 2<n<25).

26. A method for obtaining a nanosystem according to claim 23, comprising the steps of:
   a) preparing a nanosome by mixing hydroxyacids and mercaptoacids in the presence of a base in aqueous medium,
   b) adding at least one metal salt to the mixture prepared in step a), and
   c) reducing the mixture obtained in step b).

27. A method for detecting a nanosystem comprising metal atomic quantum clusters (AQCs) of at least two different sizes encapsulated in a cavity with an inner diameter less than or equal to 10 nm, said method comprising the steps of:
   a) exciting the nanosystem with an external excitation source at a predetermined excitation wavelength (λexc.), and
   b) detecting one or more of the following parameters of said nanosystem by a detection apparatus: emission wavelength (λem.); intensity; mean lifetime; anisotropy.

* * * * *